(12) United States Patent
Sreeramagiri et al.

(10) Patent No.: US 7,959,589 B2
(45) Date of Patent: Jun. 14, 2011

(54) ADJUSTABLE ORTHOTIC DEVICE

(75) Inventors: Murali Krishna Sreeramagiri, Irvine, CA (US); Brice Robertson, Rancho Santa Magarita, CA (US)

(73) Assignee: Ossur HF, Reykjavik (IS)

( * ) Notice: Subject to any disclaimer, the term of this patent is extended or adjusted under 35 U.S.C. 154(b) by 297 days.

(21) Appl. No.: 12/213,815

(22) Filed: Jun. 25, 2008

(65) Prior Publication Data

US 2009/0240181 A1 Sep. 24, 2009

Related U.S. Application Data

(63) Continuation-in-part of application No. 11/230,035, filed on Sep. 19, 2005, now Pat. No. 7,431,708.

(51) Int. Cl.
*A61F 5/00* (2006.01)
(52) U.S. Cl. .......................................... 602/16; 602/26
(58) Field of Classification Search .............. 602/20–28, 602/5, 16; 128/882
See application file for complete search history.

(56) References Cited

U.S. PATENT DOCUMENTS

| | | |
|---|---|---|
| 4,599,998 A | 7/1986 | Castillo |
| 4,856,501 A | 8/1989 | Castillo |
| 4,940,044 A | 7/1990 | Castillo |
| D318,736 S | 7/1991 | Castillo |
| 5,135,469 A | 8/1992 | Castillo |
| 5,230,697 A | 7/1993 | Castillo |
| 5,288,287 A | 2/1994 | Castillo |
| 5,302,169 A | 4/1994 | Taylor |
| D357,070 S | 4/1995 | Castillo |
| 5,792,086 A | 8/1998 | Bleau et al. |
| D433,756 S | 11/2000 | Castillo |
| 6,875,187 B2 | 4/2005 | Castillo |
| 7,037,287 B2 | 5/2006 | Cormier et al. |
| 7,156,818 B2 * | 1/2007 | Salmon et al. ............ 602/5 |
| 7,198,610 B2 | 4/2007 | Ingimundarson et al. |
| 2002/0183674 A1 | 12/2002 | Castillo |
| 2004/0127825 A1 | 7/2004 | Castillo |
| 2007/0106189 A1 | 5/2007 | Salmon et al. |

FOREIGN PATENT DOCUMENTS

WO 97/29717 8/1997

* cited by examiner

*Primary Examiner* — Michael A. Brown
(74) *Attorney, Agent, or Firm* — Bacon & Thomas, PLLC

(57) ABSTRACT

An orthotic brace includes a proximal support section pivotally connected to a distal support section, and each having a medial frame and a lateral frame connected to width adjustment plates. At least one angle adjusting component provided in the lateral or medial frames allows angular adjustment of the brace. The width adjustment plates include lateral and medial slots through which fixing members pass to engage the respective frame portions. This permits the space between the lateral frame and the medial frame to be adjusted according to the size of the wearer's body part. Proximal and distal shells are adjustably positioned on the width adjustment plates via a series of positioning holes axially arranged along the shells which selectively engage a fixing member passing through a positioning slot on the width adjustment plates. This allows for the shells to be both axially adjusted and positioned along the width of the brace.

20 Claims, 5 Drawing Sheets

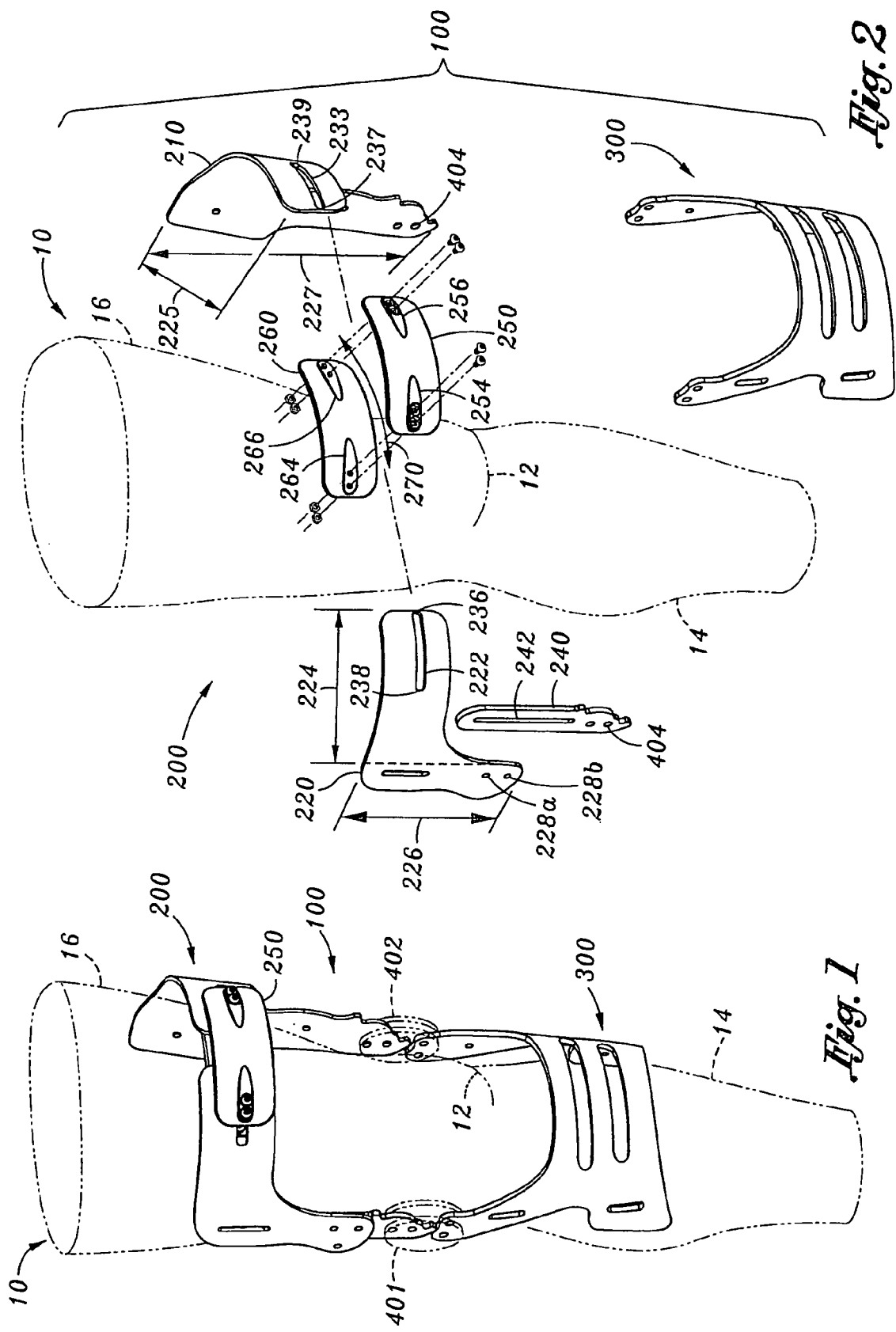

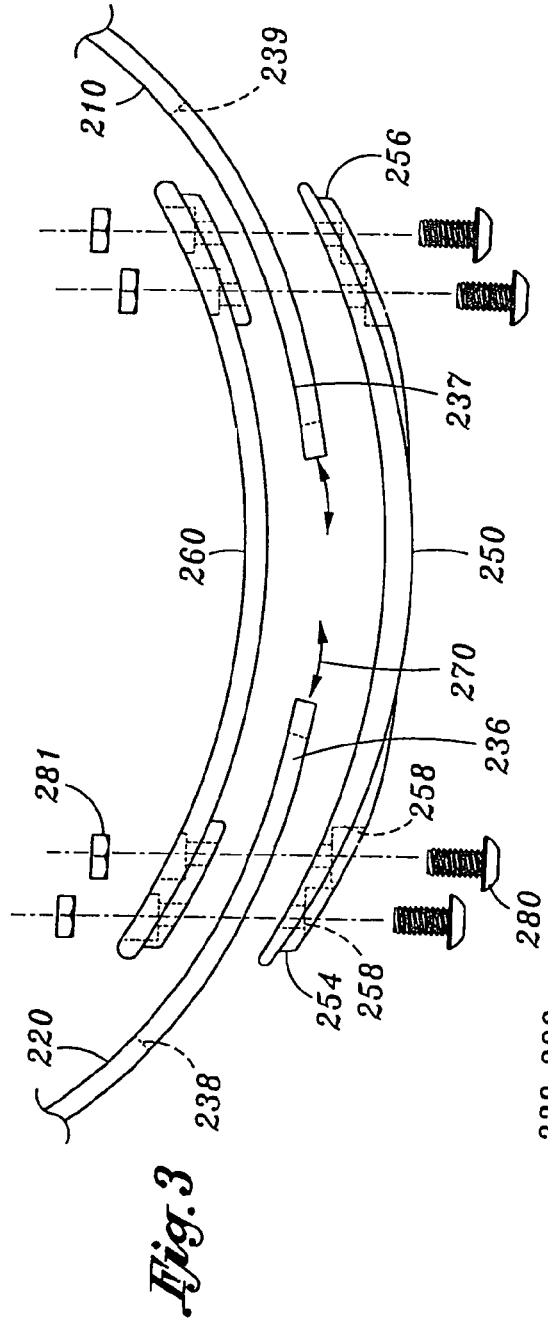
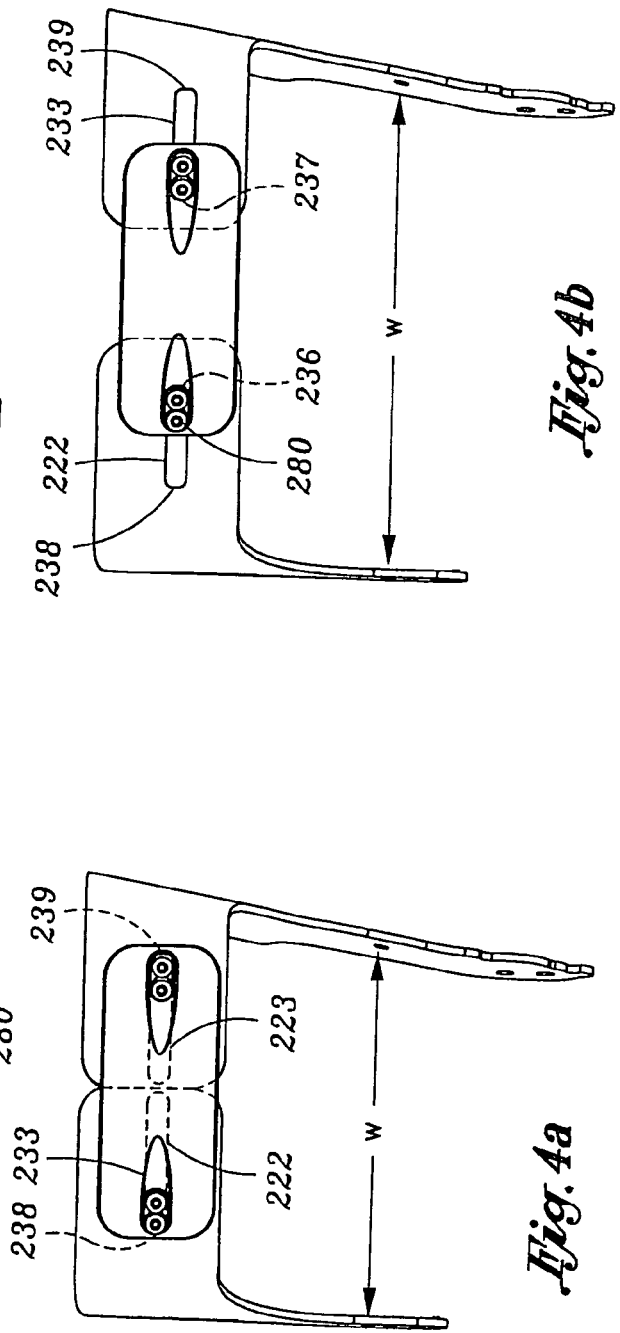

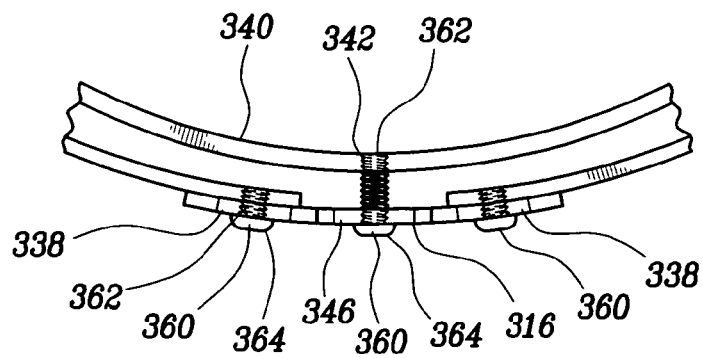
*Fig. 7*
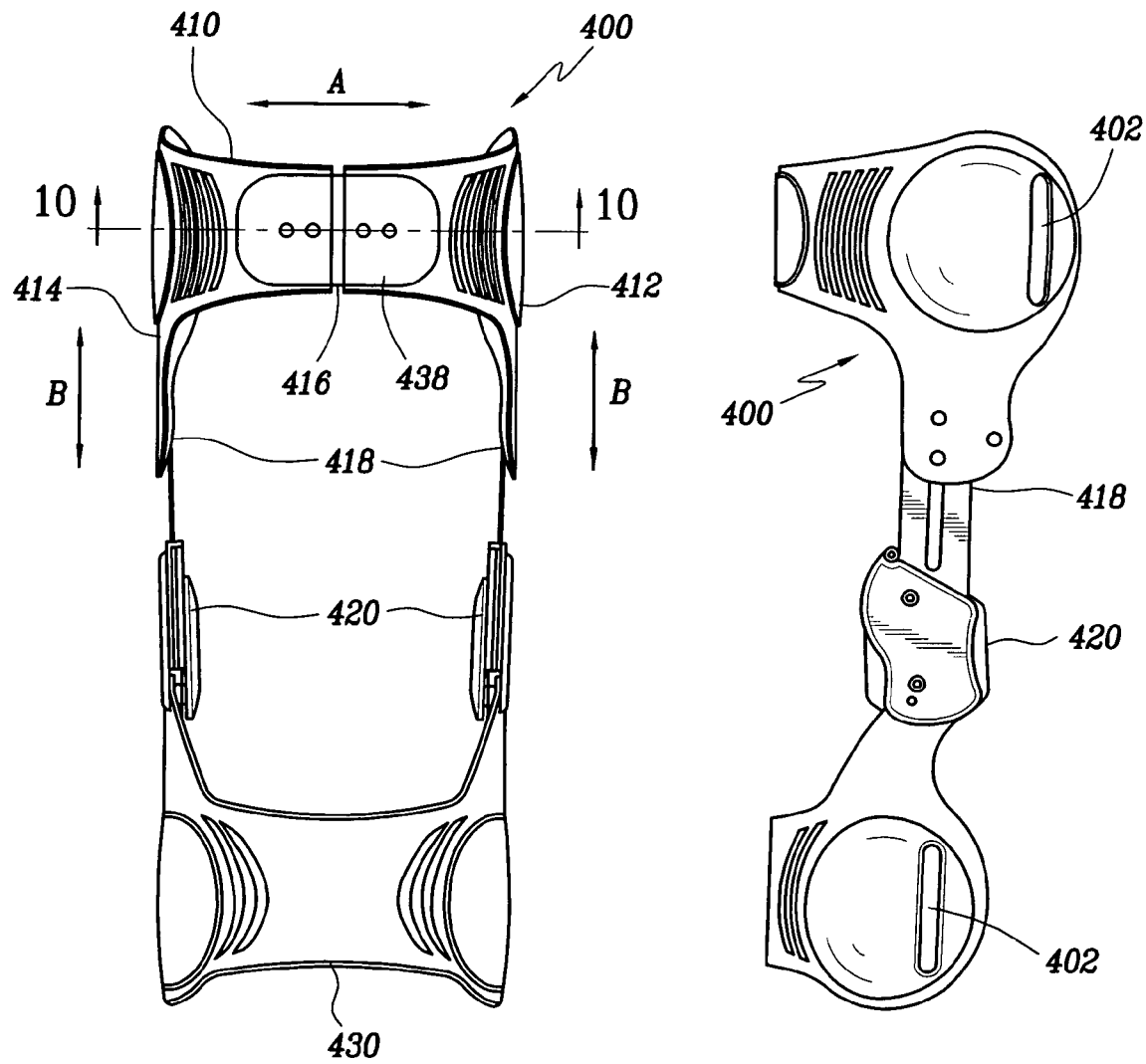
*Fig. 8*  *Fig. 9*

ADJUSTABLE ORTHOTIC DEVICE

CROSS-REFERENCE TO RELATED APPLICATIONS

This application is a continuation-in-part of prior U.S. patent application Ser. No. 11/230,035, filed Sep. 19, 2005.

BACKGROUND

1. Technical Field

The present invention relates to orthotic devices for providing support and/or therapeutic treatment to body parts, such as alleviating symptoms of osteoarthritis and other joint dysfunctions. More particularly, the present invention relates to an adjustable orthotic device, such as an adjustable knee brace for an osteoarthritic knee joint.

2. Description of the Related Art

Osteoarthritis, also known as degenerative joint disease, is the most common form of arthritis. It is believed that the disease results from a combination of genetic abnormalities and joint injuries. An affected joint progressively loses cartilage, and as a result, the tissue that lines the joint can become inflamed, the ligaments can loosen, and the associated muscles can weaken. Especially vulnerable are knee joints, where sufferers experience pain, stiffness and swelling, and become unable to perform basic life functions such as walking.

Osteoarthritis can be treated with prescription drugs, homeopathic remedies, total joint replacements, and braces. A patient suffering from osteoarthritis in the knee can be fitted with a knee brace whereby support is provided to allow reasonable ambulatory activity without undue risk of injury. Knee bracing does not cure osteoarthritis, but there are indications that the severity of the symptoms may be reduced by bracing because physical forces upon the joint are reduced.

Knee braces are frequently fitted to the exact measurements of the patient, and a properly adjusted brace can accommodate the shape, size, and angle between the femur and the tibia for maximum comfort. However, custom fit knee braces are expensive because each one must be custom manufactured to order.

In order to bring the advantages of the knee brace, namely the non-invasive treatment of osteoarthritis, to a broader spectrum of individuals, knee braces manufactured from common i.e. universal components have been developed. However, these knee braces typically cannot properly accommodate each and every different leg configuration.

Due to this problem in the art, a number of adjustable knee braces have been developed. Among the changes an osteoarthritic knee undergoes is that the body tries to compensate for the degenerative joint and migrate laterally or outwardly, or it may migrate inwardly or medially, with the former condition often referred to as "bowlegged" and the latter referred to as "knock-kneed." When either event occurs, the leg experiences a corresponding curvature, and the wearer continues to suffer pain and discomfort. In order to accommodate such a leg configuration, knee braces angularly adjustable to overcome leg curvature have been developed.

However, other parameters for adjustment have not been possible in such prior knee braces. Accordingly, a primary object of the present invention is to provide a knee brace for the treatment of osteoarthritis that is capable of accommodating a wide variety of leg widths. Another object of the present invention is to provide a knee brace capable of both width adjustment and angular adjustment for maximum comfort of the wearer. Still another object of the present invention is to provide a knee brace that is easily adjustable by the wearer or healthcare professionals. Yet another object of the present invention is to provide an adjustable knee brace that can be constructed of common, universal components so as to simplify the initial fitting as well as subsequent repairs.

BRIEF SUMMARY

An adjustable knee brace for supporting the leg of an osteoarthritic or another individual suffering from a dysfunctional knee joint is disclosed. The brace is comprised of an upper brace supporting the femur, or thigh, portion of the leg, and a lower brace supporting the tibia, or shin, portion of the leg. The upper brace and the lower brace are in a pivoting relationship about a hinge component.

The upper brace includes a lateral frame and a medial frame. The lateral frame connects directly to the hinge component, while the medial frame has an angle adjustment arm which enables the knee brace to be angularly adjusted to accommodate legs where the tibia and femur bend inwardly, or where the tibia and femur bend outwardly. The angle adjustment arm is slidably engaged to the medial frame, and in a pivoting relationship with the lower brace about the hinge component.

The width across the lateral frame and the medial frame is adjustable. A lateral frame adjustment slot and a medial frame adjustment slot is situated on the lateral frame and the medial-frame, respectively, and is in a sliding relationship with an outer width adjustment plate and an inner width adjustment plate. A retaining bolt secures the outer width adjustment plate, the lateral frame and the medial frame, and the inner width adjustment plate, in place, by a retaining nut that is threaded thereon.

By tightening the retaining bolt against the retaining nut, the lateral frame and the medial frame are secured in place, while loosening the same will permit adjustment of the lateral frame and the medial frame. This sliding adjustment enables the knee brace to accommodate a wide range of leg widths.

In an alternative embodiment, an orthotic brace includes a proximal support section pivotally connected to a distal support section at lateral and medial flexion-extension hinges. Each of the proximal and distal support sections has a medial frame and a lateral frame connected to width adjustment plates. The width adjustment plates include lateral and medial width adjusting slots through which fixing members pass to engage the respective frame portions. Thus, the space between the lateral frame and the medial frame can be adjusted according to the size of the wearer's body part. Proximal and distal shells are adjustably positioned on the width adjustment plates via a series of positioning holes axially arranged along the shells which selectively engage a fixing member passing through a positioning slot on the width adjustment plates. Thus, the shells can be both axially adjusted and positioned along the width of the brace. At least one angle adjusting component, as described above, allows angular adjustment of the brace.

In variations, the angle adjusting component can be positioned between the lateral flexion-extension hinge and the lateral component of the proximal frame. Additionally, an angle adjusting component can be positioned between the medial flexion-extension hinge and the medial component of the proximal frame.

In a further variation, the angle adjusting component can be positioned between the lateral flexion-extension hinge and the lateral component of the distal frame. Additionally, an angle adjusting component can be positioned between the medial flexion-extension hinge and the medial component of the distal frame.

In a further variation, a knee brace includes width adjusting structure incorporated with the proximal shell member, which has lateral and medial shell components and a width adjusting plate. The length and/or the varus/valgus angle of the brace can also be adjusted via axial adjusting components positioned with the lateral and medial portions of the proximal frame and lateral and medial struts connecting to flexion-extension or Range of Motion (ROM) hinges. In further variations, the width adjusting structure can be provided in the distal shell member. Additionally, the axial adjusting components can be provided both in the proximal and distal strut portions between the proximal and distal shell members and the flexion-extension/ROM hinge, respectively.

The numerous other advantages, features, and functions of embodiments of an orthotic device will become readily apparent and better understood in view of the following description and accompanying drawings. The following description is not intended to limit the scope of the orthotic device, but instead merely provides exemplary embodiments for ease of understanding.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a front perspective view of a knee brace in place on a leg, the leg and the hinge component shown in phantom;

FIG. 2 is an exploded perspective view of the knee brace shown in FIG. 1, depicted in relation to a leg, the leg shown in phantom;

FIG. 3 is an exploded top elevation view of the knee brace shown in FIG. 1;

FIG. 4a is a front view of an adjustable femoral frame fully contracted;

FIG. 4b is a front view of an adjustable femoral frame fully extended;

FIG. 7 is a top-down sectioned view of the proximal frame and shell of the embodiments of the orthotic braces shown in FIGS. 5 and 6;

FIG. 8 is a front view of a variation of an adjustable orthotic device;

FIG. 9 is a side view of the embodiment of FIG. 8; and

Figure 5:
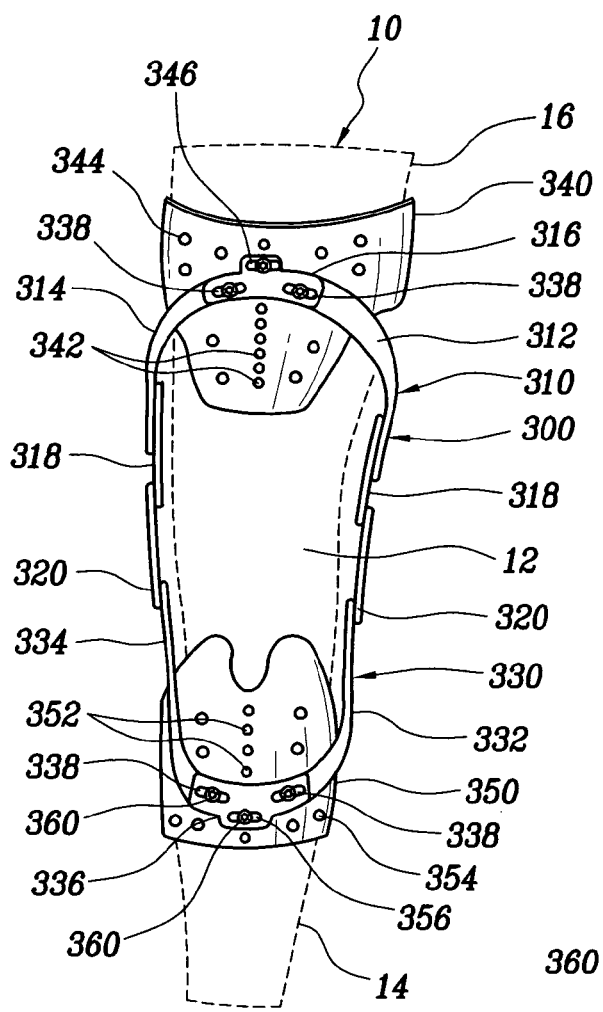
FIG. 5 is a front view of an alternate embodiment of an adjustable orthotic brace.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of a knee brace and the components thereof, and in no way limit the structures or configurations of a knee brace and components thereof according to the present disclosure.

DETAILED DESCRIPTION

A. Environment and Context

Embodiments of an orthotic device are provided to reduce the effect of osteoarthritis in a knee joint, or stabilize a knee joint that has been weakened by injury or other infirmities. It will be understood that the orthotic device may be configured to reduce or cure both medial and lateral knee joint infirmities in either the left or right knee.

The embodiments of the disclosure are particularly adapted for a human knee joint, and may be dimensioned to accommodate different types, shapes and sizes of human joints and appendages. In addition, due the adjustable design, a single orthotic device can be used to treat numerous different sizes of joints.

For explanatory purposes, the knee brace embodiments described herein are divided into sections which are denoted by general anatomical terms for the human body. Each of these terms is used in reference to a human leg which is divided in similar sections with a proximal-distal plane generally extending along the meniscus of the knee between the femur and tibia.

The embodiment of the knee brace is also divided into anterior and posterior sections by an anterior-posterior plane. The anterior-posterior plane generally corresponds to the coronal or frontal plane of a human leg. Each of the anterior and posterior sections is further divided about the center of the knee by a transverse or proximal-distal plane and median, sagittal or lateral-medial planes. Thus, the term "lateral" further has its ordinary meaning and refers to a location lying at or extending toward the right or left side, away from the median plane of the knee. Additionally, the term "medial" has its ordinary meaning and refers to a location lying or extending toward the median plane of the knee. Also, as used herein, the term "proximal" thus has its ordinary meaning and refers to a location that is closer to the heart than another location. Likewise, the term "distal" has its ordinary meaning and refers to a location that is further from the heart than another location.

The anatomical terms described herein are not intended to detract from the normal understanding of such terms as readily understood by one of ordinary skill in the art of orthotics.

B. Detailed Description of an Embodiment of an Adjustable Knee Brace

The detailed description set forth below in connection with the appended drawings is intended as a description of exemplary embodiments of the invention and is not intended to represent the only form in which the present invention may be constructed or utilized. It is to be understood, however, that the same or equivalent functions may be accomplished by different embodiments that are also intended to be encompassed within the spirit and scope of the invention.

With reference to FIGS. 1 and 2, an exemplary embodiment of an adjustable knee brace 100 with respect to a wearer's leg 10 is shown. Leg 10 is anatomically comprised of femur (thigh) section 16, knee 12, and tibia (shin) section 14. Femur section 16 is braced by femoral frame 200 and is in a pivoting relationship with tibial frame 300, which braces tibia section 14. Such a pivoting relationship is enabled by hinge components 401 and 402, which preferably are ratio swing hinges constructed according to the disclosure in U.S. Pat. No. 4,940,044, owned by the current Assignee, the disclosure of which is expressly incorporated herein in its entirety by reference. Such hinge components 401 and 402 are designed to closely simulate the rotational movement of the tibia relative the femur, and essentially simulate normal knee movements. All connections herein to hinge components 401 and 402 are as described in the referenced patent. Those skilled in the art will recognize that other conventional hinge constructions are clearly contemplated for use herein.

Referring specifically to FIG. 2, an exploded view of the knee brace 100 is shown. Femoral frame 200 is comprised of medial frame 220, lateral frame 210, inner width adjustment plate 260, and outer width adjustment plate 250.

Medial frame 220 has a horizontally elongate section 224 and vertically elongate section 226. Horizontally elongate section 224 includes a width adjustment slot 222 which extends substantially across horizontally elongate section 224. Furthermore, horizontally elongate section 224 is preferably formed in an arcuate configuration to accommodate the shape of leg 10, specifically the curvature of femur section 16 so as to minimize the profile resulting from and the obstruction caused by the presence of knee brace 100.

Vertically extending section 226 is comprised of upper angular adjustment bolt securing hole 228a, and lower angular adjustment bolt securing hole 228b. Angle adjustment arm 240 has a vertically elongate angle adjustment slot 242, which slidably engages medial frame 220 at angular adjustment bolt securing holes 228a and 228b. Angle adjustment retaining bolts (not shown) are inserted through angle adjustment holes 228a and 228b and angle adjustment slot 240. In its most extended state, the upper end of angle adjustment slot 242 corresponds in position to that of upper angular adjustment bolt securing hole 228a. In its most contracted state, the lower end of angle adjustment slot 242 corresponds in position to that of lower angular adjustment bolt securing hole 228b. Thus, the effective height of the medial side of knee brace 100 can be adjusted, and accordingly, adjustable for bow-legged and knock-kneed legs, a condition characterized by the tibia angling towards the medial-side of the leg or the lateral side of the leg. By tightening the angle adjustment retaining bolt, the position of the angle adjustment arm 240 is secured relative to the medial frame 220. An analogous angular adjustment is disclosed in U.S. Pat. No. 6,875,187, the disclosure of which is expressly incorporated by reference in its entirety herein.

Lateral frame 210, similar to its counterpart medial frame 220, has a horizontally elongate section 225 and a vertically elongate section 227. Horizontally elongate section 225 includes a width adjustment slot 233 which extends substantially across horizontally elongate section 225. Like the horizontally elongate section 224 of medial frame 220, the horizontally elongate section 225 of lateral frame 210 is preferably formed having an arcuate configuration to accommodate the shape of leg 10. Unlike medial frame 220, however, lateral frame 210 has an extended vertically elongate section to compensate in height for the lack of an angle adjustment arm. Instead, the lower end of lateral frame 210 has hinge connecting holes 404 to the hinge component 401 shown in FIG. 1, whereas the medial frame 210 has no hinge connecting holes; the hinge connecting holes 404 being on the angle adjustment arm 240.

With reference to FIGS. 2, 3, 4a, and 4b, the details of the width adjustment mechanism will be explained. Specifically referring to FIGS. 2 and 3, width adjustment slot 222 has a distal end 238 and a proximal end 236. Lateral frame 210 also has width adjustment slot 233 configured to mirror width adjustment slot 222 on medial frame 220. Lateral frame adjustment slot 222 has a proximal end 237 and a distal end 239.

Outer width adjustment plate 250 has medial extrusion 254 and lateral extrusion 256, and inner width adjustment plate 260 similarly has medial extrusion 264 and lateral extrusion 266. Medial extrusion 264 and lateral extrusion 266 of inner width adjustment plate 260 is configured to abut slightly into width adjustment slots 222 and 233 so as to facilitate a sliding relationship along semicircular horizontal axis 270 with minimal angular deviation from the same.

As illustrated in FIG. 3, medial frame 220 and lateral frame 210 is sandwiched i.e. disposed between outer width adjustment plate 250 and inner width adjustment plate 260. Outer width adjustment plate 250 and inner width adjustment plate 260 include retaining bolt securing holes 258. The sandwiched relationship is maintained by retaining bolt 280, which is passed through retaining bolt securing holes 258 on outer width adjustment plate 250, then through width adjustment slots 222 and 233 on medial frame 220 and lateral frame 210, respectively, then through retaining bolt securing holes 258 on inner width adjustment plate 260, and finally tightened with retaining nut 281. When the width configuration is determined by the user, retaining bolt 280 and retaining nut 281 is tightened to prevent further movement of medial frame 220 and lateral frame 210 against outer width adjustment plate 250 and inner width adjustment plate 260. When the width configuration is to be modified, retaining bolt 280 and retaining nut 281 is loosened.

Now referring to FIGS. 4a and 4b, the width adjustment functionality of femoral brace 200 is shown. In its most extended position as shown in FIG. 4a, retaining bolt 280 is positioned in the most inward location, proximal ends 236 and 237 of width adjustment slots 222 and 233. In its most contracted position as shown in FIG. 4b, retaining bolt 280 is positioned in the most outward location at distal ends 238 and 239 of width adjustment slots 222 and 233. As can be seen, the width 232 of femoral brace 200 can be increased or decreased depending on the relative position of the lateral frame 220 and medial frame 210 with respect to the outer and inner width adjustment plates 250 and 260 shown in FIG. 2. Thus, legs of a variety of widths can be rapidly and securely accommodated with the present inventive device.

The above description is given by way of example, and not of limitation. Given the above disclosure, one skilled in the art could devise variations that are within the scope and spirit of the invention disclosed herein. Further, the various features of the embodiments disclosed can be used alone, or in varying combinations with each other and are not intended to be limited to the specific combination described herein. Thus, the scope of the claims is not to be limited by the illustrated embodiments.

C. Detailed Description of Alternate Embodiments of an Adjustable Knee Brace

Figure 6:
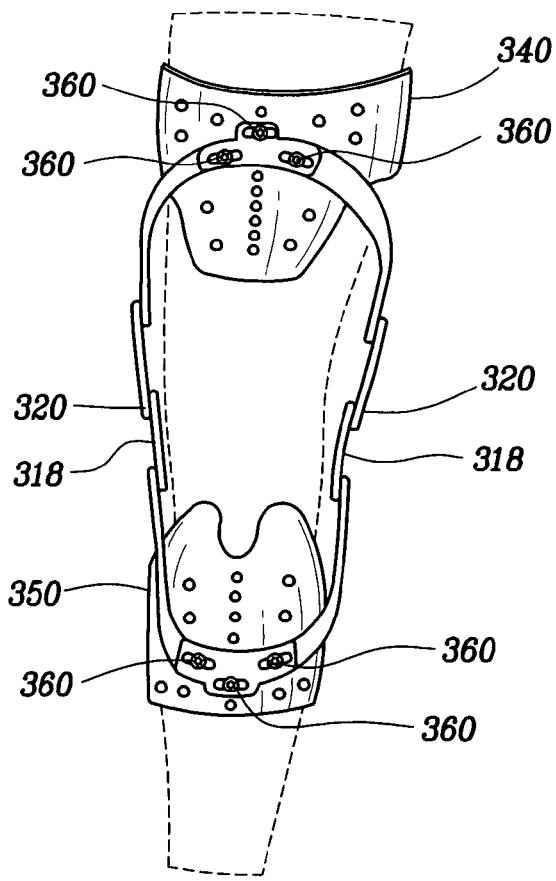
FIG. 6 is a front view of a further alternate embodiment of an adjustable orthotic brace.

Alternate embodiments of an adjustable orthotic brace are shown in FIGS. 5 and 6. The embodiments of FIGS. 5 and 6 are constructed in a very similar manner and thus a detailed description is provided only with respect to the embodiment shown in FIG. 5, and the differences in FIG. 6 are highlighted. The embodiments of FIGS. 5 and 6 describe structures associated with an off-the-shelf brace that can be utilized with any number of sizes and shapes of legs and knees due to the numerous adjustable components incorporated therewith. Such adjustability avoids the costs associated with creating custom braces for each user, or alternatively, producing large numbers of different sized braces in order to accommodate a wide variety of leg shapes and sizes. Additionally, the adjustability provides a more comfortable fit of the brace for the user, since the portions of the brace can be adjusted to closely conform and accommodate a wide variety of leg shapes and sizes.

Similarly to the previous embodiment, as shown in FIG. 5, an adjustable knee brace 300 is positioned on the leg 10. The brace 300 is configured to engage the tibia or shin section 14 of the leg 10 and the femur or thigh section 16 of the leg 10 in order to support the knee joint 12.

The knee brace 300 includes a proximal frame 310 and a distal frame 330 connected thereto via any suitable type of flexion-extension hinges 320, as discussed above in section B, and as will be recognized by a skilled artisan. Alternative hinges 320 may be of any of the types disclosed in U.S. Pat. No. 5,302,169, granted Apr. 12, 1994 or U.S. Pat. No. 7,037,287, granted May 2, 2006, and both expressly incorporated herein by reference.

The proximal frame 310 is built up of a number of components, as shown in FIG. 5. A lateral frame component 312 is arranged along the lateral side of the femur section 16. A medial frame component 314 is positioned along the medial side of the femur section 16. Each of the lateral and medial frame components 312, 314 are connected to a width adjusting plate 316, in a manner discussed below, in order to allow the width of the brace 300 to be adjusted. Additionally, an angle adjusting component 318, of the type described above, may be positioned between either or both of the lateral and medial frame components 312, 314 and the lateral and medial hinges 320.

These angle adjusting components 318 function in the manner previously described to allow the angle of the brace to be adjusted for use with users having different and varying degrees of bow-leggedness or knock-kneedness, in contrast to creating custom fit braces or numerous braces having different angles. The angle adjusting components 318 may also be used in conjunction, if provided on both the lateral and medial sides, to lengthen the brace 300 in the axial or proximal-distal direction, in order to provide length adjustment of the brace 300 for use with numerous different lengths of legs in contrast to creating custom fit braces or numerous braces having different lengths.

Similarly, the distal frame 330 includes a lateral frame component 332 positioned along the lateral side of the tibia section 14 and a medial frame component 334 positioned along the medial side of the tibia section 14. Again, the lateral and medial frame components 332, 334 are connected to a width adjusting plate 336, in the same manner as discussed below, in order to allow the width of the brace 300 to be adjusted. In this manner, a single brace can be utilized to accommodate a wide variety of legs having different widths, thus eliminating the need for creating custom braces or providing a large number of braces having different fixed widths to accommodate different size legs. Further, fixed frame braces do not provide accommodation for different states of swelling of the leg, and thus, numerous braces may be required throughout the therapeutic treatment of a single user's leg, unlike the single disclosed brace which can accommodate changes in the size of the user's leg.

As shown in the variation of FIG. 6, an angle adjusting component 318, of the type described above, may be positioned between either or both of the lateral and medial frame components 332, 334 and the lateral and medial hinges 320 in order to provide either angle or axial adjustment as previously discussed. It will be recognized that a single angle adjusting component 318 can be provided for either the proximal or distal frame, as described above in section B. As discussed above, the angle adjusting component 318 allows a single brace to be utilized for many different sized legs or varying conditions of bow-leggedness and knock-kneedness.

Each of the width adjusting plates 316, 336 include frame width adjusting slots 338 defined along the lateral and medial portions of the plates. Fixing members 360, such as threaded machine screws, bolts, or any other suitable fasteners, are provided to pass through the width adjusting slots 338 to engage the frame components 312, 314, 332, 334 in order to selectively position the frame components with respect to the respective width adjusting plates 316, 336.

The fixing members 360, as shown in FIG. 7, function in the same manner for each of the width adjusting plates and the frame components. In the illustrated embodiment, the fixing members include a threaded stem portion 362 and a head portion 364. The threaded stem portion 362 has a diameter that is smaller than the size of the width adjusting slot 338 so that the stem portion 362 can pass therethrough. The threaded stem portion 362 is configured to engage a threaded hole in the respective frame component, or to pass through a hole in the frame component to engage a threaded nut positioned behind the frame component. When the fixing member 360 is tightened, the head portion 364 is configured to engage the surfaces of the width adjusting plates or slots in order to fix the frame components in position relative thereto.

In order to adjust the width of the brace 300, the fixing members 360 are loosened so that they may slide within the width adjusting slots 338. In this manner, the positions of the frame components with respect to the width adjusting plates can be varied in order adjust the width of the brace 300. Thus, a single brace can be utilized for a wide variety of widths of legs, and the need for custom braces or a large number of braces having different widths is eliminated. Once the appropriate positions are determined, the fixing members 360 can be retightened so that the head portions 364 engage the width adjusting plates in order to fix the positions of the frame components. This width adjustment can be repeated as necessary to adjust the width of the brace to accommodate different sizes of legs or users. As an alternative, the configuration of two width adjusting plates, as described above in relation to the embodiment of FIGS. 1-4, can be utilized.

In addition to the width adjusting slots 338, as shown in FIGS. 5-7, the width adjusting plates 316, 336 also include a shell positioning slot 346, 356. The shell position slots 346, 356 are arranged to engage respective proximal and distal shell or cuff portions 340, 350 for providing additional adjustment of the brace via the relative positions of the shells with respect to the frame components.

The proximal shell 340 is configured to wrap around and engage the femur section 16 of the leg 10. The distal shell 350 is configured to wrap around and engage the tibia section 14 of the leg 10. Exemplary forms and methods of construction of the shells are described in U.S. Pat. No. 7,198,610, granted Apr. 3, 2007 and expressly incorporated herein by reference. The shells 340, 350 can include appropriate slots, D-rings, or other attachment points for straps having hook and loop fasteners, buckles, snaps, or any other suitable arrangement for tightening and fastening the shells to the leg 10 of the user, as will recognized by a skilled artisan.

Each of the shells 340, 350 include holes 344, 354 defined therein that may be utilized to provide ventilation between the shells and the leg. Each of the shells 340, 350 also include a series of axially spaced positioning holes 342, 352 defined therein. The positioning holes 342, 352 may be internally threaded to receive the threaded stem portion 362 of the fixing members 360. Alternatively, the positioning holes 342, 352 may be configured to receive a threaded nut therein, which threaded nut is configured to receive the threaded stem portion 362 of the fixing members 360.

As shown in reference to FIG. 7, the threaded stem portion 362 of the fixing member 360 passes through the shell positioning slot 346 in the width adjustment plate 316. The axial position of the proximal shell 340 is adjusted by selecting the desired positioning hole 342 for engagement with the threaded stem portion 362 of the fixing member 360. The proximal shell can be adjusted axially by selecting a more proximal or a more distal positioning hole 342. The lateral-medial position of the shell cane be adjusted in the same manner as discussed above for adjusting the width of the brace 300 by tightening and loosening the fixing member 360 so that the head portion 364 engages and disengages the surfaces of the shell positioning slot 346. The positioning of the distal shell 350 with the shell positioning slot 356 functions in the same manner and is not further described.

From the above description, it can be seen that the shells 340, 350 can be adjusted in position in both the lateral-medial, or width direction, and the axial direction. In this manner, a single brace 300 can be utilized to be appropriately fit to many different shapes and sizes of legs, and to accommodate changes in swelling of the leg during different stages of recovery from an injury. This adjustable positioning of the shells also provides a more comfortable fit, since the frames can be moved with respect to the shells such that the frames are spaced from the leg so that no contact between the leg and the frames occurs during any orientation of the leg and the brace. Again, this adjustability eliminates the need for the creation of custom fit braces or for a large number of different sized braces.

Thus, in view of the above description, a multi adjustable orthotic brace is described, which allows the width of the brace to be adjusted, the length of the brace to be adjusted, and the angle of the brace to be adjusted in order to provide a single off-the-shelf brace that is capable of use with many different sizes and shapes of legs, without the need for custom fit braces or a large number of different sized braces.

D. Detailed Description of a Variation of an Adjustable Knee Brace

Figure 10:
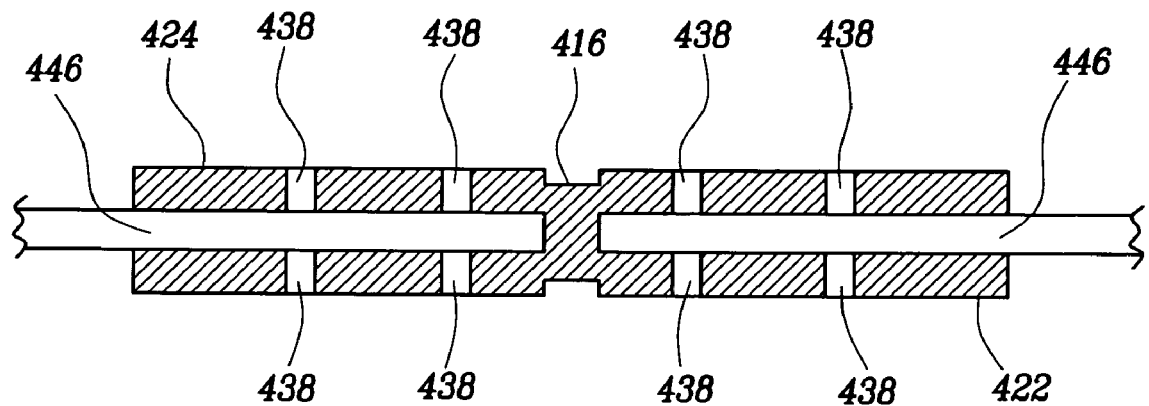
FIG. 10 is a partial cross-sectional view taken along line 10-10 of FIG. 8.

A variation of an adjustable knee brace 400 is shown in FIGS. 8-10. The knee brace 400 can be constructed of similar materials and components as those described above.

The knee brace 400 includes structures to provide for width adjustment A of the femoral or proximal shell member 410, and structures 418 to provide for axial length adjustment B and/or varus/valgus angle adjustment. In this manner, the knee brace 400 can be utilized with a variety of different sized and shaped legs and knee joints, without the need for custom manufacturing or providing numerous different sizes of the knee brace.

The knee brace 400 generally includes a femoral or proximal shell member 410 and a tibial or distal shell member 430. The shell members are pivotally connected to each other via axially extending support struts and flexion-extension or ROM hinges 420.

The proximal shell member 410 includes lateral and medial components 412, 414, which each include a strap slot 402 for retaining a strap member (not shown) therein. A width adjusting plate 416 is positioned between the lateral and medial components 412, 414 in order to provide width adjustment in a manner discussed below.

Axial adjustment components 418 of the type previously discussed are positioned between the lateral and medial proximal shell components 412, 414 and the lateral and medial hinges 420. They provide axial length adjustment or varus/valgus angle adjustment of the knee brace 400 in the manner discussed above. In an alternate configuration, additional axial adjustment components can be provided between the hinges 420 and the lateral and medial components of the distal shell 430.

As best shown in FIG. 10, the width adjustment plate 416 includes width adjusting holes 438 extending through anterior and posterior flanges 422, 424, through which fixing members (not shown) of the type described above can be inserted. The anterior and posterior flanges 422, 424 each have lateral and medial flange members that are cantilevered from a central portion of the width adjusting plate 416. Each of the lateral and medial components of the proximal shell 412, 414 also include a shell positioning slot 446, through which the fixing members pass.

In use, the fixing members can be tightened or loosened in a similar manner as described above, such that the anterior and posterior flanges of the width adjusting plate 416 either provide a compression force to the lateral and medial shell components 412, 414, or allow the lateral and medial shell components 412, 414 to slide between the anterior and posterior flanges of the width adjusting plate 416. Accordingly, the width of the proximal shell member 410 can be adjusted. Of course, a similar structure can also be provided to the distal shell 430 member in order to provide width adjustment of the distal shell member 430.

E. Conclusion

The components of the adjustable orthotic brace described herein may be formed in any suitable manner recognized by a skilled artisan, such as casting, machining, stereolithography, or any other suitable process.

The disclosed embodiments of an orthotic device provide an improved knee brace that allows for multiple adjustments in order to be appropriately sized to fit any different number of users. Additionally, it is understood that the size of the brace and the components thereof can also be adjusted so that an even larger number of different users having different sized joints and body parts may benefit from the present design.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct a knee brace in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. An adjustable orthotic brace for accommodating a variety of sizes of a wearer's anatomy and stages of recovery from an injury, the brace comprising:
   a proximal frame portion having a proximal width adjustment plate and lateral and medial frame portions adjustably connected thereto;
   a distal frame portion having a distal width adjustment plate lateral and medial frame portions adjustably connected thereto;

lateral and medial hinges respectively positioned between the proximal and distal lateral frame portions and the proximal and distal medial frame portions; and proximal and distal shells adjustably connected to the respective proximal and distal width adjustment plates, and configured to engage respective portions of anatomy of a wearer;

wherein the proximal lateral and medial frame portions are positionable relative to the proximal width adjustment plate, and the distal lateral and medial frame portions are positionable relative to the distal width adjustment plate, to adjust the width of the brace; and wherein the proximal and distal shells are positionable relative to the proximal and distal width adjustment plates, respectively, to adjust the fit and the length of the brace.

2. The adjustable orthotic brace according to claim 1, further comprising:

an angle adjusting component arranged between the medial hinge and either the proximal or distal medial frame portions to provide angular and axial adjustment of the brace.

3. The adjustable orthotic brace according to claim 2, further comprising:

an angle adjusting component arranged between the lateral hinge and either the proximal or distal lateral frame portions to provide angular and axial adjustment of the brace.

4. The adjustable orthotic brace according to claim 3, wherein the angle adjusting components define an angle adjustment slot configured to receive one or more angle adjustment retainers facilitating a sliding relationship with an angle adjusting arm.

5. The adjustable orthotic brace according to claim 4, wherein the angle adjusting arms are connected to or formed with the respective lateral and medial hinges.

6. The adjustable orthotic brace according to claim 1, further comprising:

an angle adjusting component arranged between the lateral hinge and either the proximal or distal lateral frame portions to provide angular and axial adjustment of the brace.

7. The adjustable orthotic brace according to claim 6, wherein the angle adjusting component defines an angle adjustment slot configured to receive one or more angle adjustment retainers facilitating a sliding relationship with an angle adjusting arm.

8. The adjustable orthotic brace according to claim 7, wherein the angle adjusting arm is connected to or formed with the lateral hinge.

9. The adjustable orthotic brace according to claim 1, wherein the proximal and distal width adjustment plates each define lateral and medial width adjusting slots.

10. The adjustable orthotic brace according to claim 9, further comprising an adjustable fixing member configured to pass through each respective width adjusting slot, and selectively fixing the respective proximal or distal, lateral or medial frame portion;

wherein the fixing members are slidable within the respective width adjusting slot to allow the respective frame portion to move with respect to the respective width adjustment plate to provide width adjustment of the brace.

11. The adjustable orthotic brace according to claim 1, wherein the proximal and distal width adjustment plates each define a shell positioning slot; and the proximal and distal shells each define a series of axially spaced positioning holes.

12. The adjustable orthotic brace according to claim 11, further comprising an adjustable fixing member configured to pass through each respective positioning slot, and selectively engaging one of the series of positioning holes in the proximal and distal shells to provide axial adjustability of the shells with respect to the width adjustment plates;

wherein the fixing members are slidable within the respective shell positioning slot to allow the respect shell to move with respect to the respective width adjustment plate to provide adjustable positioning of the shells.

13. An adjustable knee brace for accommodating a variety of leg sizes and stages of recovery from an injury, the brace comprising:

a proximal frame portion having lateral and medial frame portions adjustably connected to a proximal width adjustment plate;

a distal frame portion having lateral and medial frame portions adjustably connected to a distal width adjustment plate;

lateral and medial hinges respectively positioned between the proximal and distal lateral frame portions and the proximal and distal medial frame portions; and proximal and distal shells adjustably connected to the respective proximal and distal width adjustment plates, and configured to respectively engage thigh and shin sections of a wearer;

wherein the proximal and distal width adjustment plates each define a shell positioning slot; and the proximal and distal shells each define a series of axially spaced positioning holes;

wherein the proximal lateral and medial frame portions are positionable relative to the proximal width adjustment plate, and the distal lateral and medial frame portions are positionable relative to the distal width adjustment plate, to adjust the width of the brace; and wherein the proximal and distal shells are positionable relative to the proximal and distal width adjustment plates, respectively, to adjust the fit and the length of the brace.

14. The adjustable knee brace according to claim 13, further comprising:

an angle adjusting component arranged between the medial hinge and the proximal medial frame portion to provide angular and axial adjustment of the brace.

15. The adjustable knee brace according to claim 14, wherein the angle adjusting component defines an angle adjustment slot configured to receive one or more angle adjustment retainers facilitating a sliding relationship with an angle adjusting arm.

16. The adjustable knee brace according to claim 15, wherein the angle adjusting arm is connected to or formed with the medial hinge.

17. The adjustable orthotic brace according to claim 13, wherein the proximal and distal width adjustment plates each define lateral and medial width adjusting slots.

18. The adjustable orthotic brace according to claim 17, further comprising an adjustable fixing member configured to pass through each respective width adjusting slot, and selectively fixing the respective proximal or distal, lateral or medial frame portion;

wherein the fixing members are slidable within the respective width adjusting slot to allow the respective frame portion to move with respect to the respective width adjustment plate to provide width adjustment of the brace.

19. The adjustable orthotic brace according to claim 13, further comprising an adjustable fixing member configured to pass through each respective positioning slot, and selectively engaging one of the series of positioning holes in the proximal and distal shells to provide axial adjustability of the shells with respect to the width adjustment plates;

wherein the fixing members are slidable within the respective shell positioning slot to allow the respect shell to move with respect to the respective width adjustment plate to provide adjustable positioning of the shells.

20. An adjustable orthotic brace for accommodating a variety of sizes of a wearer's anatomy and stages of recovery from an injury, the brace comprising:

a proximal shell member having a width adjustment plate and lateral and medial shell components adjustably connected thereto, the width adjustment plate having anterior and posterior flanges, each having at least one positioning hole defined therethrough and aligned with first and second width adjustment slots defined respectively in the lateral and medial shell components;

a distal shell member;

the proximal lateral shell component and the proximal medial shell component movably connected to the distal shell member; and wherein the proximal lateral and medial shell components are selectively positionable relative to the width adjustment plate to adjust the width of the brace.

\* \* \* \* \*